United States Patent [19]

Moll

[11] Patent Number: 4,725,275

[45] Date of Patent: * Feb. 16, 1988

[54] ARTIFICIAL HEART VALVE

[75] Inventor: Jacek Moll, Lodz, Poland

[73] Assignee: Peter Maroko, Cherry Hill, N.J.; a part interest

[*] Notice: The portion of the term of this patent subsequent to Apr. 28, 2004 has been disclaimed.

[21] Appl. No.: 671,471

[22] Filed: Nov. 14, 1984

Related U.S. Application Data

[63] Continuation-in-part of Ser. No. 540,025, Oct. 7, 1983, Pat. No. 4,661,106.

[51] Int. Cl.$^4$ .............................................. A61F 2/24
[52] U.S. Cl. ........................................................ 623/2
[58] Field of Search .................... 3/1.5, DIG. 3; 623/2

[56] References Cited

U.S. PATENT DOCUMENTS

| | | | |
|---|---|---|---|
| 3,476,143 | 11/1969 | Kastes | 3/1.5 |
| 3,824,629 | 7/1974 | Shiley | 3/DIG. 3 |
| 4,057,857 | 11/1977 | Fettel | 3/1.5 |

Primary Examiner—Richard J. Apley
Assistant Examiner—James Prizant
Attorney, Agent, or Firm—Weiser & Stapler

[57] ABSTRACT

A heart valve having a disc (10) pivotally mounted within a ring (14) by means of projections (16, 18 and 20) carried by the ring. The disc and ring are arranged so that the blood flows through the valve as the disc moves relative to the ring so as to reduce the likelihood of blood clot formations, in turn, reducing the likelihood of thrombosis.

38 Claims, 12 Drawing Figures

ARTIFICIAL HEART VALVE

RELATED CASE

The present application is a continuation-in-part of prior copending patent application Ser. No. 540,025, filed Oct. 7, 1983, now U.S. Pat. No. 4,661,106.

TECHNICAL FIELD

The present invention relates, in general, to prostheses devices and, in particular, to an artificial heart valve for implantation in humans for replacement of damaged heart valves.

BACKGROUND ART

It is well known to replace damaged human heart valves with prostheses devices having movable vanes, flaps or balls which allow blood flow in one direction and prevent blood flow back in the opposite direction. Many different designs based on a variety of concepts have been suggested with a large number the subject of United States patents.

The present invention is directed to an artifical heart valve of the type having a vane in the form of a disc which is pivotally mounted within a base in the form of a ring. The heart valve described and illustrated in U.S. Pat. No. 3,476,143 to Kaster is typical of this type of unit. In such heart valves, the vane is hemodynamically opened (when it is in the aortic or pulmonic orifice, respectively) by systolic contraction of the ventricles of the heart which forces blood against the vane. At the onset of diastole, the pressure in the ventricles drops towards zero and the pressure of the blood in the aorta or pulmonary artery acts in a reverse direction on the vane causing it to close. In the mitral or tricuspid position, the valve is opened during diastole when blood pressure in the atrium is higher than in the ventricle, and is closed during ventricular systole when the pressure in the ventricle exceeds that of the atrium.

Besides pivotal movement, the vane is arranged to undergo rotational and translatory movements. By permitting the vane to rotate about its axis and to float within its base, the likelihood of blood clot formations at the pivot points of the vane is reduced, thereby reducing the likelihood of thrombosis. The importance of this feature is set out in U.S. Pat. No. 4,057,857 to Fettel. The present invention is directed to an artificial heart valve which provides increased float of the vane to reduce even more the likelihood of thrombosis, regardless of the position it is located in the heart, namely the mitral, tricuspid, pulmonic or aortic positions.

For a discussion of the Omniscience Cardiac Valve Prosthesis, which is an improvement over the Lillehei-Kaster valve (which has been in general use since 1971), reference is made to Omniscience Cardiac Valve Prosthesis Clinical Review 1, by R. A. Dewall, and A. A. Mikhail. For an evaluation in-vitro of the valve, see Scientific Evaluation of In-Vitro Performance of the Omniscience Cardiac Valve by Huffstutler, a paper presented at the 34th Annual Conference on Engineering in Medicine and Biology (Houston, September 1981). Another report about the valve is found in Analytical Design Fundamentals of the Omniscience Cardiac-Valve Prosthesis by Huffstutler, presented at the ASTM Symposium in Phoenix, May 1981. A state of the art review is found in Loss of Pressure for Valve-Opening Surface of the Bjork-Shiley/cc-Omniscience-, by J. Kohler, G. Ehrentraut, B. Stormer, RWTH Aachen in April, 1981 at the Annual Conference of the German Association for Heart and Circulatory Research in Bad Nauheim.

DISCLOSURE OF THE INVENTION

Accordingly it is an object of the present invention to provide a new and improved artificial heart valve.

It is another object of the present invention to provide an artificial heart valve arranged for increased float of the vane within its base to reduce the likelihood of thrombosis.

It is still another object of the present invention to provide a heart valve which presents minimum resistance to blood flow through the valve.

It is yet another object of the present invention to provide a heart valve which produces a minimal amount of turbulence in the blood flow.

Another special object of the present invention is to provide an artificial heart valve which is particularly well suited for being positioned in the mitral or tricuspid position.

Since the gradient of blood pressure between atrium and ventricle during diastole is significantly less than the pressure during systole between the ventricle and aorta or pulmonary artery, it is particularly advantageous to use the heart valve of the invention in the mitral or tricuspid position because this valve offers so little resistance to blood flow.

It is therefore another object of the invention to reduce resistance to flow in the mitral or tricuspid position.

A further object achieved by the construction of the valve of the invention is that it permits for a greater distance between the disc and the ring of the valve (as further described below). This provides an improved "washing effect" by the blood stream and therefore further decreases the likelihood of thrombosis.

BRIEF DESCRIPTION OF DRAWINGS

Referring to the drawings.

In the several views provided, like reference numbers denote similar structure.

BEST MODE OF CARRYING OUT THE INVENTION

Figure 1:
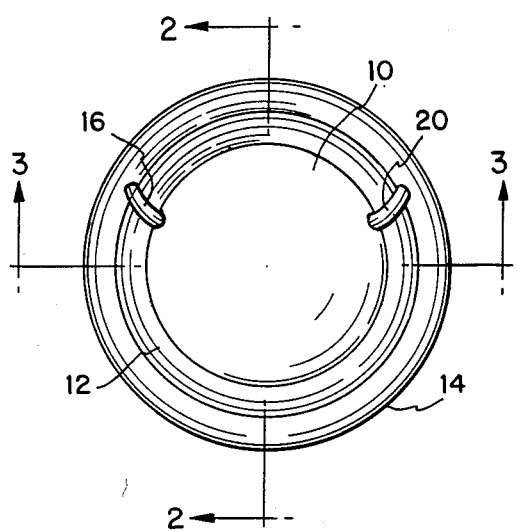
FIG. 1 is a plan view of a heart valve constructed in accordance with the present invention, with the heart valve closed.

Referring to FIGS. 1 through 7, one embodiment of a heart valve constructed in accordance with the present invention includes a disc 10 having a circumferential ridge 12 on one face of the disc. The outside surface 12a of ridge 12 forms a convex peripheral edge on the disc and the inside surface 12b is sloped. This is shown most clearly in the sectional views of FIGS. 2, 3 and 5. For the embodiment of the invention illustrated, inside surface 12b of ridge 12 has a straight-line slope of less than seventy degrees from the rotation axis of disc 10, preferably on the order of ten to forty degrees.

Disc 10 has a convexo-concave configuration having radial symmetry about its rotation axis which is perpendicular to the general plane of the disc. The face of disc 10 having ridge 12 is convex and faces downstream of the blood flow. Hereinafter, this face will be referred to as the distal surface. The opposite face of disc 10 is concave and faces upstream of the blood flow. Hereinafter, this face will be referred to as the proximal surface.

A heart valve constructed in accordance with the present invention also includes a ring 14 within which disc 10 is retained. Ring 14 has an inside surface 14a which is convex and defines the valve orifice through which blood flows as controlled by the movement of disc 10. Specifically, disc 10 is retained in ring 14 for pivotal movement of the disc by two angularly spaced projections 16, 20, and one radially spaced projection 18 which serves as a pivoting surface. Projections 16 and 20 extend around ridge 12 and will be referred to hereinafter as prongs 16 and 20. Prongs 16, 20 are spaced apart angularly on a chord preferably having a length of from one-third to two-thirds of the diameter of ring 14. The ends of prongs 16, 20 are rounded, and are preferably spherical. Projection 18 is positioned diametrically and has a length greater than one-half the diameter of ring 14, preferably two-thirds of the diameter of the ring.

Figure 2:
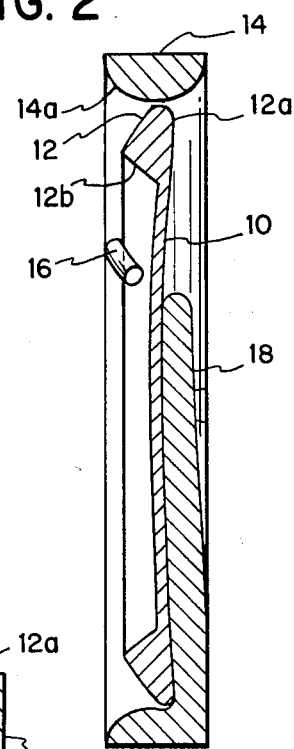
FIG. 2 is a sectional view, on an enlarged scale, taken along line 2—2 of FIG. 1.
Figure 3:
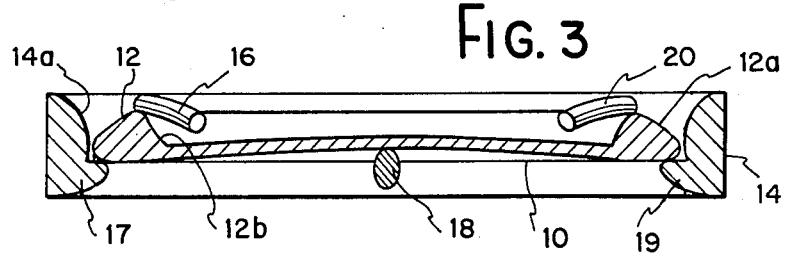
FIG. 3 is a sectional view, on an enlarged scale, taken along line 3—3 of FIG. 1.
Figure 4:
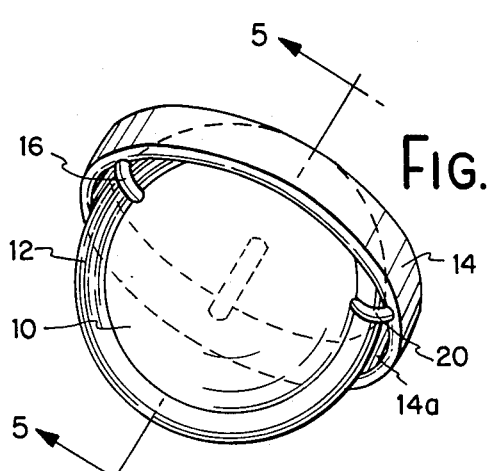
FIG. 4 is a perspective view of a heart valve constructed in accordance with the present invention, with the heart valve partially open.
Figure 5:
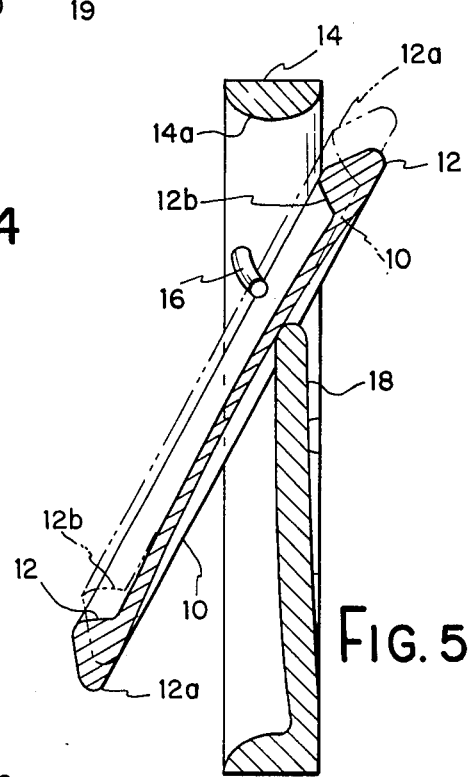
FIG. 5 is a sectional view, on an enlarged scale, taken along line 5—5 of FIG. 4.
Figure 6:
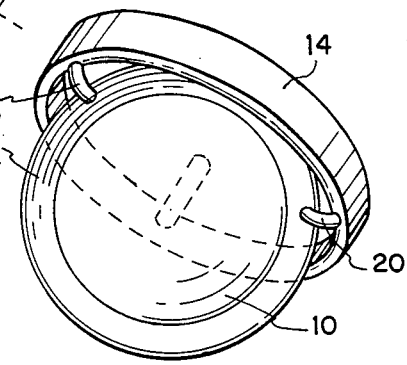
FIG. 6 is a perspective view, similar to FIG. 4, with the disc of the valve displaced from its position in FIG. 4.
Figure 7:
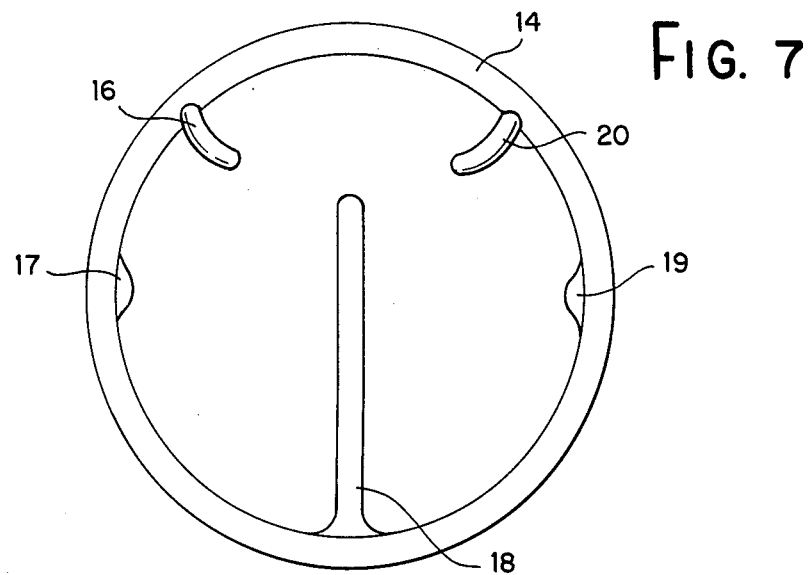
FIG. 7 is a plan view of a heart valve constructed in accordance with the present invention, with the disc of the valve omitted.

The arrangement of prongs 16 and 20, projection 18 and disc 10 permits movement of the disc from a closed position, illustrated in FIGS. 1, 2 and 3, in which the disc is contained within ring 14, and an open position in which the disc is at an angle less than ninety degrees from the closed position, to open the valve orifice. Preferably, disc 10 is retained in ring 14 to permit the disc to open to an angle of approximately eighty degrees from the closed position. If the movement of disc 10 is permitted to approach a position perpendicular to the closed position, the tendency for the valve to remain open during diastole increases because blood flow in the reverse direction can cause the disc to remain in the open position instead of forcing the disc back to the closed position. FIGS. 4, 5 and 6 illustrate a partially open valve with disc 10 at an intermediate pivotal position.

Prongs 16 and 20, at the distal surface face of disc 10, extend around ridge 12 with the ends of these projections spaced from that portion of the distal surface bounded by the ridge. Projection 18, at the proximal surface face of disc 10, extends over the proximal surface of the disc. The heart valve may be assembled by positioning disc 10 within ring 14 and then bending the projections to captivate the disc within the ring. Pivot 18 together with stops 17 and 19 serves as a rest for disc 10 when it is in the closed position.

As described, disc 10 is able to undergo three degrees of movement relative to ring 14. First, disc 10 pivots between the open and closed positions of the valve. Second, disc 10 can rotate about its rotation axis. Third, disc 10 can float relative to ring 14 in that it can undergo translatory movements in the general plane of the disc. This last degree of movement is particularly important in reducing the likelihood of blood clot formations in the region of prongs 16, 20 and projection 18, at which disc 10 is retained by ring 14.

The highly desirable feature of added translatory movement of disc 10 is achieved through the combination of the following construction details. Prongs 16 and 20 are spaced from the surface bounded by ridge 12 so that disc 10 is able to move until the ends of prongs 16 and 20 engage sloped surface 12b at its top. This is shown most clearly by comparing the position of disc 10 in FIG. 4 with the position of the disc in FIG. 6. Likewise, the solid-line position of disc 10 in FIG. 5 shows the engagement of prong 16 with the top of sloped surface 12b, while the broken-line position of the disc shows the disc in closer proximity to ring 14.

Also, by contouring the peripheral edge 12a of disc 10 and the inside surface 14a of ring 14 to each be convex, these surfaces diverge from one another in the region at which the disc is retained by the ring, thereby providing added space for translatory movement of the disc relative to the ring. For the embodiment of the invention illustrated in FIGS. 1 through 7, surface 14a of ring 14 is circular and the center of curvature of surface 14a is in the plane containing the outermost points of surface 12a of disc 10. As a result, as disc 10 pivots from the closed position shown in FIG. 2 to the partially open position shown in FIG. 5, the radially outermost portion of surface 12a has added space to clear the radially innermost portion of surface 14a than if one or both of these surfaces was flat. The space between ring surface 14a and disc surface 12a permits the blood flowing in the region at which the disc is retained by the ring to "wash" the valve surfaces and reduce the liklelihood of clot formations in this region.

In addition, by providing a ridge on only one face of disc 10 instead of on both faces, more translatory movement is achieved than if a ridge is formed on both faces. This is achieved by forming the proximal surface so that the concave surface is a portion of a sphere which extends to the periphery of the disc.

Figure 8:
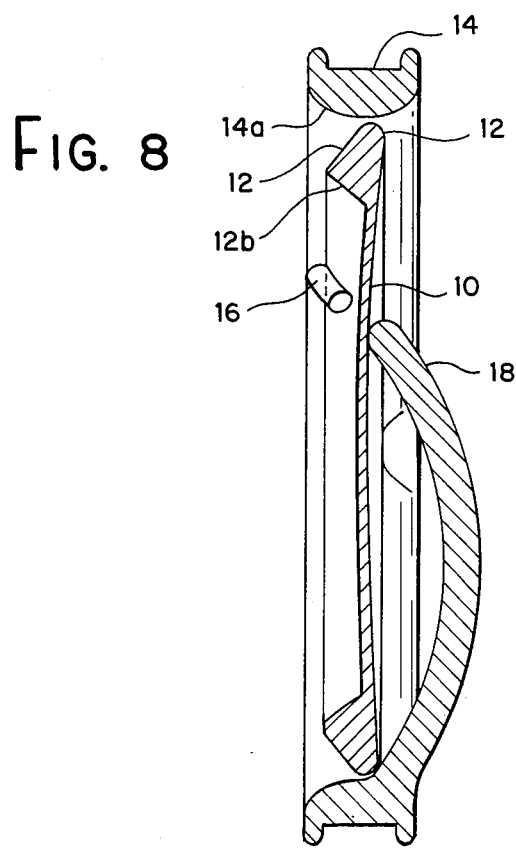
FIG. 8 is a sectional view, similar to FIG. 2, showing an alternative embodiment heart valve constructed in accordance with the present invention.

FIG. 8 illustrates another embodiment of a heart valve constructed in accordance with the present invention. This embodiment is generally similar to the first embodiment, except that the projection 18 is differently shaped.

Figure 9:
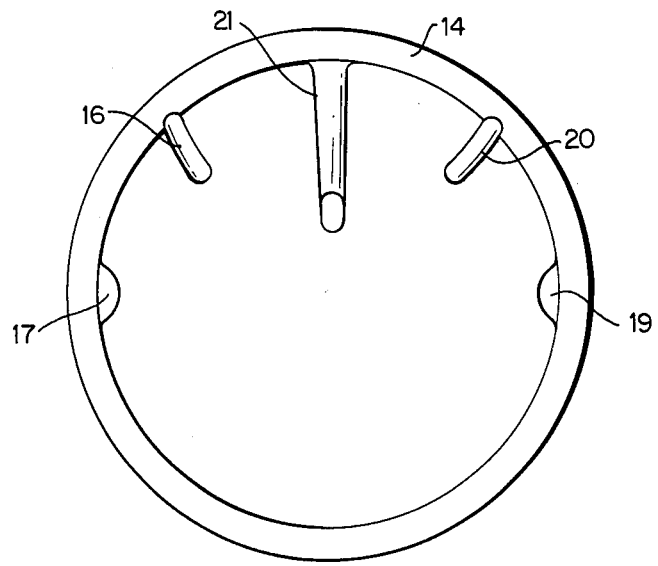
FIG. 9 is a plan view, similar to FIG. 7, showing another alternative embodiment heart valve constructed in accordance with the present invention.
Figure 10:
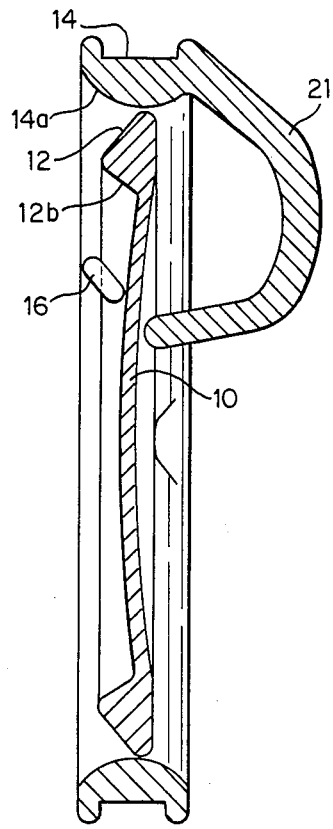
FIG. 10 is a sectional view, similar to FIG. 2, of the alternative embodiment heart valve of FIG. 9.

FIGS. 9 and 10 illustrate yet another embodiment of a heart valve constructed in accordance with the present invention. This embodiment is also generally similar to the first embodiment, except that the projection 21 extends outwardly from the ring 14 as shown, from a position which is approximately midway between the prongs 16 and 20.

Figure 11:
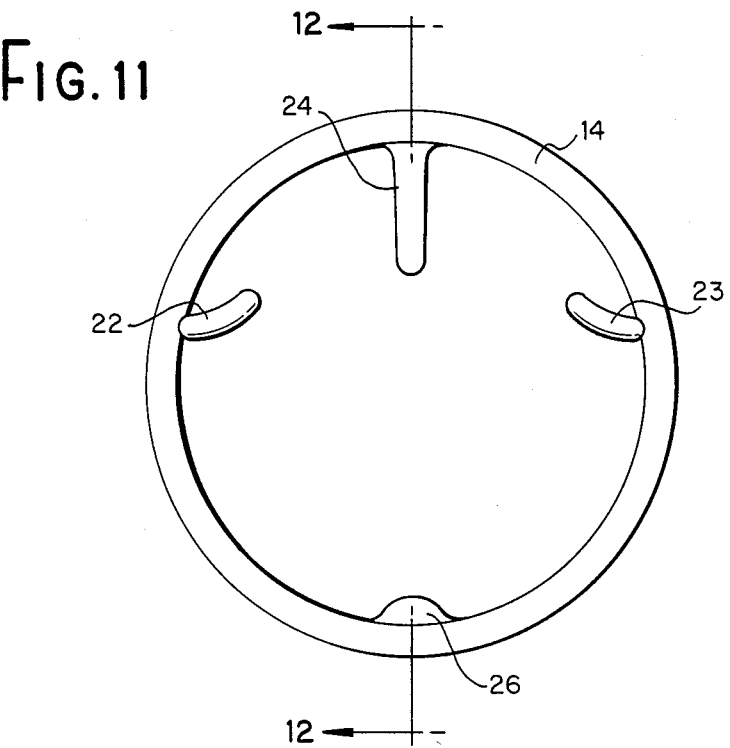
FIG. 11 is a plan view, similar to FIG. 7, showing a further alternative embodiment heart valve constructed in accordance with the present invention.
Figure 12:
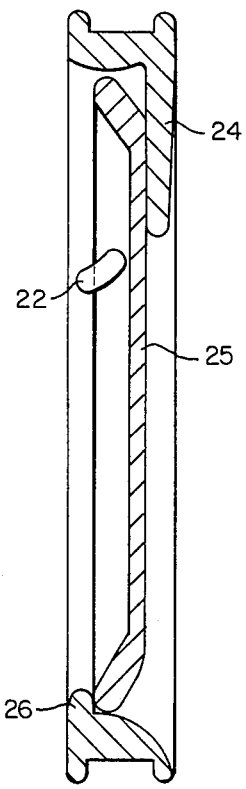
FIG. 12 is a sectional view, similar to FIG. 2, of the alternative embodiment heart valve of FIG. 11.

FIGS. 11 and 12 illustrate still another embodiment of a heart valve constructed in accordance with the present invention. This embodiment is again essentially similar to the first embodiment, but incorporates several structural differences. For example, the prongs 22 and 23 are correspondingly positioned somewhat closer to the center axis of the ring 14 than were the prongs 16 and 20 previously described. The projection 24 extends generally radially inwardly from a position which is approximately midway between the prongs 22 and 23 to a position which approaches the cord which connects the ends of the prongs 22 and 23, and a single stop 26 is positioned diametrically opposite to the projection 24. The disc 25 has essentially planar faces, and a dish-shaped rim which projects away from the projection 24 for engagement by the prongs 22 and 23.

Accordingly, while in the foregoing there has been described a preferred embodiment of the present invention, it should be understood to those skilled in the art that various modifications and changes can be made without departing from the true spirit and scope of the present invention as recited in the claims.

What is claimed:

1. A heart valve comprising:
   a disc having opposing faces and a marginal ridge formed on a first face, the outside surface of said ridge forming a convex peripheral edge on said disc and the inside surface of said ridge being a straight line sloped surface; and
   a ring having a convex inside surface within which said disc is retained by two angularly spaced and one radially disposed projection for pivotal movement of said disc between a closed position in which said disc is contained within said ring to close off the opening of said ring and an open position in which said disc is at an angle less than ninety degrees from said closed position to open said opening of said ring, said pair of angularly spaced projections extending around said marginal ridge on said disc with the ends of said angularly spaced projections spaced from the surface of said disc and positioned immediately adjacent to said marginal ridge to engage said inside surface of said ridge upon translatory movement of said disc, and said radially disposed projection extending only partially across said opening of said ring and over a second face of said disc opposite the first face, to permit said disc to rotate about its axis relative to said ring.

2. A heart valve according to claim 1 wherein the straight line sloped surface and the convex peripheral edge of said marginal ridge are connected by a straight line sloped surface.

3. A heart valve according to claim 1 wherein said slope is at an angle of less than seventy degrees from the rotation axis of said disc.

4. a heart valve according to claim 3 wherein said slope is not less than ten degrees and not more than forty degrees.

5. A heart valve according to claim 1 wherein said angularly spaced projections extend radially from said ring at an angle to said radius.

6. A heart valve according to claim 1 wherein said angularly spaced projections define a cord between the ends thereof, and wherein said radially disposed projection terminates substantially along said cord.

7. A heart valve according to claim 1 wherein ends of the angularly spaced projections are rounded.

8. A heart valve according to claim 10 wherein said ends are spherical.

9. A heart valve according to claim 1 wherein the surfaces of said first face and said second face are essentially planar.

10. A heart valve according to claim 1 wherein said projections extend only partaily across the opening defined by said ring.

11. A heart valve according to claim 10 wherein said angularly spaced projections overlie only the marginal ridge of said disc.

12. A heart valve according to claim 1 wherein only a single radially disposed projection extends over the second face of said disc.

13. A heart valve according to claim 1 wherein said angle is not more than eighty degrees.

14. A heart valve according to claim 1 wherein only said first face of said disc has a marginal ridge.

15. A heart valve according to claim 1 wherein said ring incorporates stop means adapted to engage peripheral portions of said disc in said closed position.

16. A heart valve according to claim 15 wherein said stop means comprises a pair of diametrically opposed stops.

17. A heart valve according to claim 15 wherein said stop means is positioned diametrically opposite to said radially disposed projection.

18. A heart valve according to claim 1 wherein the surface of said first face of said disc is convex and the surface of said second face of said disc is concave.

19. A heart valve according to claim 18 wherein said inside surface of said ring is circular and the center of curvature of said circular surface lies in the plane containing the outermost points of said peripheral edge of said disc.

20. A heart valve according to claim 18 wherein said concave surface extends to the periphery of said disc.

21. A heart valve according to claim 20 wherein said concave surface is a portion of a sphere.

22. A heart valve according to claim 18 wherein the first and second faces of said disc are portions of a sphere and are parallel to each other.

23. A heart valve according to claim 18 wherein the outside surface of said ridge is circular.

24. A heart valve according to claim 1 wherein said radially disposed projection is diametrically disposed in said ring.

25. A heart valve according to claim 24 wherein said angularly spaced projections are positioned on opposite sides of said radially disposed projection.

26. A heart valve according to claim 25 wherein said angularly spaced projections are symmetrically disposed about said radially disposed projection.

27. A heart valve according to claim 26 wherein said radially disposed projection extends from said ring at a position which is between said angularly spaced projections.

28. A heart valve according to claim 27 wherein the length of said radially disposed projection is equal to less than one-half of the diameter of said ring.

29. A heart valve according to claim 28 wherein the length of said radially disposed projection is equal to about one-third of the diameter of said ring.

30. A heart valve according to claim 27 wherein said radially disposed projection is substantially coplanar with said ring.

31. A heart valve according to claim 27 wherein said radially disposed projection bows outwardly from the plane of said ring.

32. A heart valve according to claim 26 wherein said radially disposed projection extends from said ring at a position which is remote from said angularly spaced projections.

33. A heart valve according to claim 32 wherein the length of said radially disposed projection is equal to at least one-half of the diameter of said ring.

34. A heart valve according to claim 33 wherein the length of said radially disposed projection is equal to about two-thirds of the diameter of said ring.

35. A heart valve according to claim 32 wherein said radially disposed projection is substantially coplanar with said ring.

36. A heart valve according to claim 32 wherein said radially disposed projection bows outwardly from the plane of said ring.

37. A heart valve comprising:
a disc having a first face which is convex and a second face which is concave, and a marginal ridge formed only on said first face of said disc, the outside surface of said ridge forming a convex peripheral edge on said disc and the inside surface of said ridge being a straight line sloped surface; and
a ring having a convex inside surface within which said disc is retained by two angularly spaced and one radially disposed projection for pivotal movement of said disc between a closed position in which said disc is contained within said ring to close off the opening of said ring and an open position in which said disc is at an angle less than ninety degrees from said closed position to open said opening of said ring, said pair of angularly spaced projections extending around said marginal ridge on said disc with the ends of said angularly spaced projections spaced from the surface of said disc and positioned immediately adjacent to said marginal ridge to engage said inside surface of said ridge upon translatory movement of said disc, and said radially disposed projection extending only partially across said opening of said ring and over a second face of said disc opposite the first face, to permit said disc to rotate about its axis relative to said ring.

38. A heart valve comprising:
a disc having a first, convex face which is a portion of a sphere and a second, concave face which is a portion of a sphere and which is parallel to the first face, and a marginal ridge formed only on said first face of said disc, the outside surface of said ridge being circular and forming a convex peripheral edge on said disc and the inside surface of said ridge being a straight line surface sloped at an angle of from ten degrees to forty degrees from the rotation axis of said disc; and
a ring having a convex inside surface which is circular and with a center of curvature which lies in the plane containing the outermost points of the peripheral edge of said disc, within which said disc is retained by two angularly spaced projections which extend radially from said ring, at an angle to said radius, and a single radially disposed projection, to permit pivotal movement of said disc between a closed position in which said disc is contained within said ring to close off the opening of said ring and an open position in which said disc is at an angle less than ninety degrees from said closed position to open said opening of said ring, said pair of angularly spaced projections extending around said marginal ridge on said disc to overlie only said marginal ridge, with the ends of said angularly spaced projections spaced from the surface of said disc and positioned immediately adjacent to said marginal ridge to engage said inside surface of said ridge upon translatory movement of said disc, and said radially disposed projection extending only partially across said opening of said ring and over a second face of said disc opposite the first face, to permit said disc to rotate about its axis relative to said ring.

* * * * *